(12) United States Patent
Chuang et al.

(10) Patent No.: US 10,847,049 B2
(45) Date of Patent: Nov. 24, 2020

(54) INTERACTIVE SERVICE PLATFORM AND OPERATING METHOD THEREOF

(71) Applicant: PixArt Imaging Inc., Hsin-Chu County (TW)

(72) Inventors: Chih-Yuan Chuang, Hsin-Chu County (TW); Yen-Min Chang, Hsin-Chu County (TW)

(73) Assignee: PIXART IMAGING INC., Hsin-Chu County (TW)

( * ) Notice: Subject to any disclaimer, the term of this patent is extended or adjusted under 35 U.S.C. 154(b) by 448 days.

(21) Appl. No.: 15/285,574

(22) Filed: Oct. 5, 2016

(65) Prior Publication Data

US 2017/0236441 A1 Aug. 17, 2017

(30) Foreign Application Priority Data

Feb. 17, 2016 (TW) .............................. 105104570 A

(51) Int. Cl.
| G09B 11/00 | (2006.01) |
| A61B 5/16 | (2006.01) |
| A61B 5/024 | (2006.01) |
| A61B 5/1455 | (2006.01) |
| A61B 5/08 | (2006.01) |
| A61B 5/021 | (2006.01) |

(Continued)

(52) U.S. Cl.
CPC ............ *G09B 11/00* (2013.01); *A61B 5/0022* (2013.01); *A61B 5/021* (2013.01); *A61B 5/02416* (2013.01); *A61B 5/0816* (2013.01); *A61B 5/14551* (2013.01); *A61B 5/165* (2013.01); *A61B 5/7239* (2013.01); *A61B 5/7264* (2013.01); *G09B 5/02* (2013.01); *G09B 7/02* (2013.01); *G09B 19/00* (2013.01)

(58) Field of Classification Search
CPC . G06F 19/3475; G06F 19/3481; G16H 15/00; G16H 50/50; A61B 5/165; A61B 5/0816; A61B 5/7239; A61B 5/7264; A61B 5/14551
See application file for complete search history.

(56) References Cited

U.S. PATENT DOCUMENTS 6,331,162 B1 * 12/2001 Mitchell ............ A61B 5/02125
600/485
8,862,448 B2 * 10/2014 Holmes ............... G06F 19/3437
703/6

(Continued)

FOREIGN PATENT DOCUMENTS

| CN | 103917993 A | 7/2014 |
| TW | 200741594 A | 11/2007 |

(Continued)

*Primary Examiner* — James B Hull
(74) *Attorney, Agent, or Firm* — Hauptman Ham, LLP

(57) ABSTRACT

An operating method of an interactive service platform including the steps of: communicating with a plurality of user end devices via an application software; receiving physiological measurement information of user from the user end devices via the application software; analyzing the physiological measurement information to identify a physical and mental state/lifestyle of an associated subscriber; and automatically responding content information associated with at least one associated subscriber according to requests from the user end devices.

22 Claims, 6 Drawing Sheets

(51) Int. Cl.
*A61B 5/00* (2006.01)
*G09B 5/02* (2006.01)
*G09B 7/02* (2006.01)
*G09B 19/00* (2006.01)

(56) References Cited

U.S. PATENT DOCUMENTS

| | | | | |
|---|---|---|---|---|
| 9,460,263 | B2* | 10/2016 | Holmes | G06F 19/3437 |
| 2004/0225225 | A1* | 11/2004 | Naumov | A61B 5/02416 |
| | | | | 600/507 |
| 2006/0123138 | A1* | 6/2006 | Perdomo | G06F 1/1626 |
| | | | | 710/2 |
| 2011/0059422 | A1* | 3/2011 | Masaoka | G06Q 30/02 |
| | | | | 434/157 |
| 2014/0143064 | A1* | 5/2014 | Tran | A61B 5/0022 |
| | | | | 705/14.66 |
| 2017/0053091 | A1* | 2/2017 | Holmes | G06F 19/3437 |
| 2017/0080346 | A1* | 3/2017 | Abbas | A63F 13/825 |

FOREIGN PATENT DOCUMENTS

| | | |
|---|---|---|
| TW | 200904079 A | 1/2009 |
| TW | 201324192 A1 | 6/2013 |

* cited by examiner

INTERACTIVE SERVICE PLATFORM AND OPERATING METHOD THEREOF

CROSS REFERENCE TO RELATED APPLICATION

This application claims the priority benefit of Taiwan Patent Application Serial Number 105104570, filed on Feb. 17, 2016, the full disclosures of which are incorporated herein by reference.

BACKGROUND

1. Field of the Disclosure

This disclosure generally relates to a service platform installed on a server system, more particularly, to an interactive service platform based on user's physiological characteristics and an operating method thereof.

2. Description of the Related Art

The conventional social application and on-line service platform do not have the function of analyzing a current physical and mental state of a user according to the user's physiological characteristics.

Accordingly, the present disclosure provides an on-line interactive service platform which identifies the current physical and mental state/lifestyle of associated subscribers according to the user's physiological characteristics, and actively provides, according to requests from user end devices, content information associated with at least one subscriber. By using the interactive service platform of the present disclosure, it is possible to effectively improve the understanding between platform's subscribers.

SUMMARY

The present disclosure provides an interactive service system, an interactive service platform and an operating method thereof that analyze physiological measurement information of subscribers such as the blood oxygenation, heart rate, respiration rate, blood pressure and second derivative of photoplethysmogram (SDPPG) using photoplethysmography signals (PPG signals), and accordingly identify at least one of the current physiological state, current emotion state and lifestyle of the subscribers.

The present disclosure further provides an interactive service system, an interactive service platform and an operating method thereof that analyze the authorized subscriber's personal data by using the text mining to accordingly identify at least one of the personality and favorite (likes and dislikes) of members.

The present disclosure provides an operating method of an interactive service platform. The interactive service platform is installed on a server system connecting to an internet. The operating method includes the steps of communicating, by application software, between the interactive service platform and a plurality of user end devices via the internet; receiving, by the interactive service platform, physiological measurement information provided by the user end devices via the internet using the application software; analyzing, by the interactive service platform, the physiological measurement information to identify at least one of a physiological state, an emotion state and a lifestyle of associated subscribers; and actively responding, according to requests from the user end devices, content information of at least one subscriber based on an analyzed result of the physiological measurement information associated with the at least one subscriber.

The present disclosure further provides an interactive service platform which is installed on a server system connecting to an internet. The interactive service platform includes a communication module, a feature analysis module, a database and a dialogue module. The communication module is configured to communicate with a plurality of user end devices via the internet to receive requests and photoplethysmography signals from the user end devices, and send content information to the user end devices. The feature analysis module is configured to analyze the photoplethysmography signals to identify at least one of a physiological state, an emotion state and a lifestyle of associated subscribers. The database is configured to store photoplethysmography signals of a plurality of subscribers and an analyzed result of the photoplethysmography signals corresponding to each of the subscribers. The dialogue module is configured to actively respond, according to the requests from the user end devices, the content information of at least one subscriber based on the analyzed result of the photoplethysmography signals associated with the at least one subscriber.

The present disclosure further provides an interactive service system including a plurality of user end devices and an interactive service platform. The interactive service platform is installed on a server system connecting to an internet, and configured to receive, by application software, physiological measurement information from the user end devices via the internet, analyze the physiological measurement information to identify a physical and mental state as well as a lifestyle of associated subscribers, actively respond, according to requests of the user end devices, content information of at least one subscriber based on an analyzed result of the physiological measurement information associated with the at least one subscriber.

The present disclosure provides an operating method of an interactive service platform. The interactive service platform is installed on a server system connecting to an internet. The operating method includes the steps of: communicating, by application software, between the interactive service platform and a plurality of user end devices via the internet; receiving, by the interactive service platform, autonomic inputted subscriber's personal data provided by the user end devices via the internet using the application software; and automatically exchanging the autonomic inputted subscriber's personal data between two user end devices among the plurality of user end devices when the two user end devices become authorized subscribers of each other.

The subscriber's personal data of the present disclosure includes, for example, information of various digital content associated with subscribers on social networking sites, communication software, game dialogue, contacts, positioning systems, visited websites, search keywords, emails, pictures, contributions and papers outside the interactive service platform, but not limited thereto.

In the present disclosure, an interactive service platform actively responding content information is referred to that the interactive service platform has previously acquired the permission of associated subscribers (e.g., through a subscriber setting screen) such that when the interactive service platform receives requests from other subscribers, the interactive service platform actively responds the requests of the other subscribers directly according to analyzed results without a real-time permission given by the associated subscribers again.

In some embodiments, a response of the interactive service platform is the analyzed result but not the actual response of a user associated with an inquired subscriber. In addition, in other embodiments, the interactive service platform is possible to be arranged to real-timely inform the requests from the other subscribers to the user associated with the inquired subscriber and to accordingly forward a response of the user.

The interactive service platform of the present disclosure is applicable to various network service platform connected to a network such as a gaming platform, dating platform, a social application platform, a communication software platform and so on.

BRIEF DESCRIPTION OF THE DRAWINGS

Other objects, advantages, and novel features of the present disclosure will become more apparent from the following detailed description when taken in conjunction with the accompanying drawings.

DETAILED DESCRIPTION OF THE EMBODIMENT

It should be noted that, wherever possible, the same reference numbers will be used throughout the drawings to refer to the same or like parts.

Figure 1:
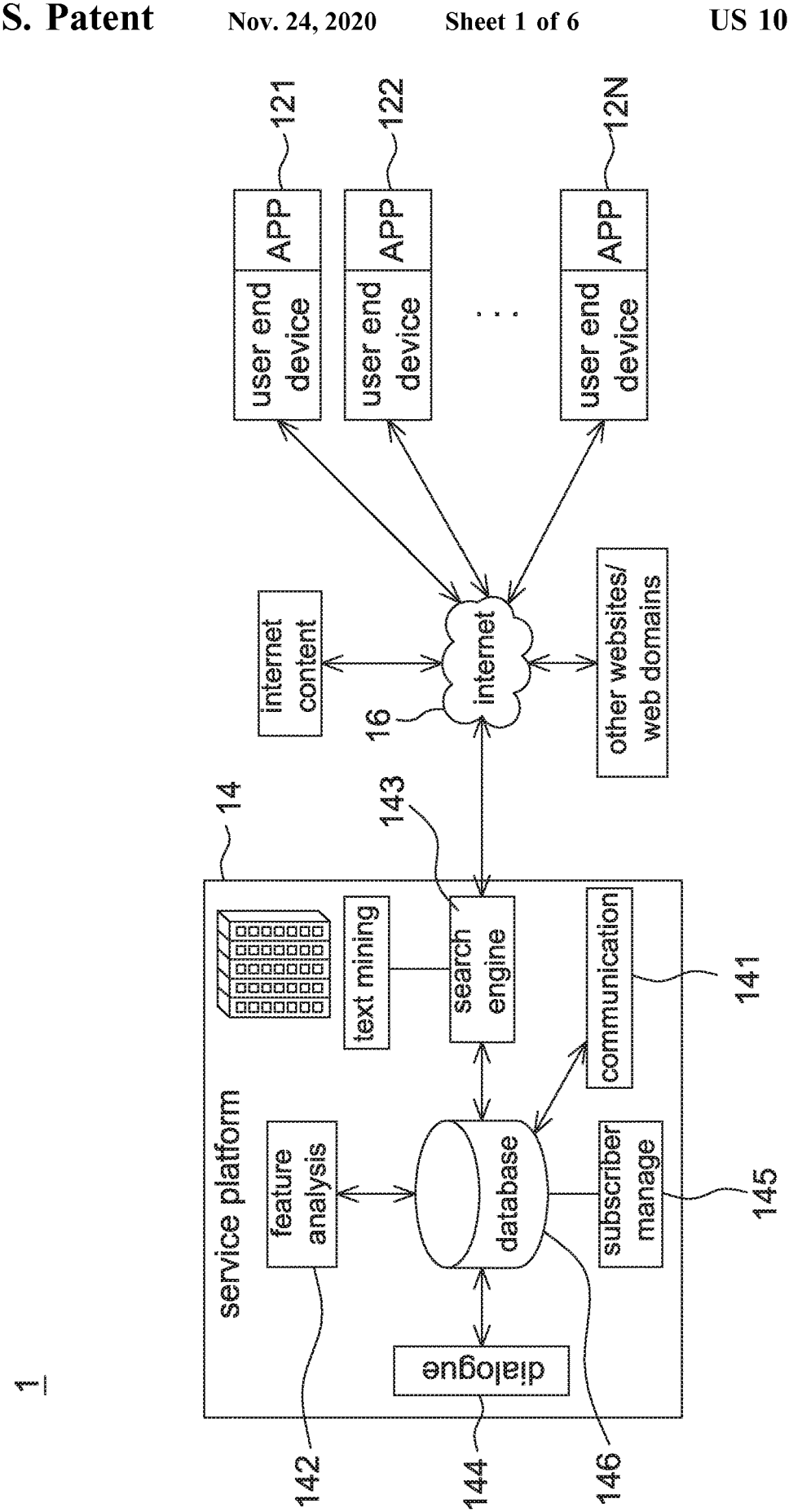
FIG. 1 is a schematic diagram of an on-line interactive service system according to one embodiment of the present disclosure.

Referring to FIG. 1, it is a schematic diagram of an on-line interactive service system according to one embodiment of the present disclosure. The interactive service system 1 includes a plurality of user end devices 121-12N and an interactive service platform 14 connected together via an internet 16. The interactive service platform 14 is installed on a server system connected to the internet 16. The interactive service platform 14 receives, using application software (APP), physiological measurement information from the user end devices 121-12N via the internet 16, wherein the internet 16 includes the physical network and wireless communication network.

The interactive service platform 14 analyzes the received physiological measurement information to identify a physical and mental state/lifestyle (e.g., at least one of a physiological state, an emotion state and a lifestyle, but not limited to) of associated subscribers, and actively responds, according to requests of the user end devices 121-12N, content information of at least one subscriber based on an analyzed result of the physiological measurement information associated with the at least one subscriber. For example, each user end device may request the interactive service platform 14 to reply analyzed and identified results of its own subscriber or other subscribers to be served as the content information.

The user end devices 121-12N are, for example, portable electronic devices, wearable electronic devices, fixed devices, equipment or apparatus wired or wirelessly coupled to the network 16 without particular limitations, e.g., including a smart watch, a bracelet, a foot ring, an earphone, glasses, a smart phone, a personal digital assistance (PDA), a notebook, a work station, a tablet computer, a smart home appliance, a navigation device or the like.

In some embodiments, the physiological measurement information includes at least one of a photoplethysmography (PPG) signal and a voiceprint data. For example, when the user end devices 121-12N are telephone devices, the application software (APP) is able to automatically acquire the voiceprint through user's talking and convert the voiceprint to an audio file to be transmitted to the interactive service platform 14 via the internet 16.

In some embodiments, the user end devices 121-12N are built in with the physiological measuring function for measuring the physiological measurement information, and provide the measured physiological measurement information to the interactive service platform 14 via the internet 16.

In some embodiments, the user end devices 121-12N themselves do not have the physiological measuring function but are wired or wirelessly coupled to a physiological detection device for wired or wirelessly receiving the physiological measurement information from the physiological detection device, and provide the received physiological measurement information to the interactive service platform 14 via the internet 16.

In some embodiments, analyzing the physiological measurement information includes analyzing the PPG signal to obtain a value variation and/or timeline feature of physiological characteristics, such as the value variation and timeline feature of at least one of a blood oxygenation, a heart rate, a respiration rate, a blood pressure and a second derivative of photoplethysmogram (SDPPG).

For example, if the user end devices 121-12N are able to detect the PPG signal, the user end devices 121-12N may include at least one light source and a light sensing element. The at least one light source is used to illuminate a skin surface of a user to cause light beams to go through skin tissues under the skin surface. The light sensing element is a light emitting diode or an image sensor array for detecting ejected light from the skin tissues and generating PPG signals.

The detection of physiological characteristics may be referred to U.S. patent application Ser. Nos. 14/685,782, 14/728,051, 14/825,272, 14/847,143 and TW Patent Application Numbers TW 105100804, TW 105102395 assigned to the same assignee of the present disclosure, and the full disclosures of which are incorporated herein by reference.

In other embodiments, analyzing the physiological measurement information further includes analyzing the rising and falling of voiceprint data to accordingly obtain a value variation and/or timeline feature of the voiceprint data.

As the value variation and/or timeline feature of the physiological measurement information can change with conditions of a user, the value variation and/or timeline feature may reflect a current physical and mental state as well as lifestyle of the user.

Said value variation includes, for example, an increment or decrement of physiological values as well as a ratio of the increment or decrement. For example, when a user is under different states such as exercising, sleeping, excited, falling ill, tired and so on, the measured values of the PPG signal and voiceprint data with time reflect corresponded states.

Said timeline feature includes, for example, the distribution of the above states at different times within a day and a week. For example, corresponding to the time that subscribers go to bed and wake up each day as well as do exercise in a week, the measured PPG signal and voiceprint data reflect a value distribution at these times. For example, within a timeline of doing exercise, the respiration rate, heart rate, blood oxygenation and blood pressure may maintain at relatively higher values. For example, within a timeline of sleeping, the respiration rate, heart rate, blood oxygenation and blood pressure may maintain at relatively lower values. In addition, within a timeline of frilling ill, being tired and being excited, the physiological measurement information has its unique feature. By analyzing the relationship between said unique feature and each state, it is possible to build up a corresponding relationship of the value variation and/or timeline feature to every state to accordingly classify subscribers and identify a state of subscribers.

In order to obtain the above value variation and timeline feature, the interactive service platform 14 receives the physiological measurement information from the user end devices 121-12N continuously or every a predetermined time interval via the internet 16, wherein the predetermined time interval may be fixed or non-fixed without particular limitations. Accordingly, the interactive service platform 14 may classify subscribers, e.g., a type of early hours, night owls, sports, otaku and so on, by long-term monitoring and analyzing physiological measurement information of every subscriber as a part of the analyzed results of analyzing the physiological measurement information.

Referring to FIG. 1 again, in one embodiment, the interactive service platform 14 includes a communication module 141, a feature analysis module 142, a search engine 143, a dialogue module 144, a subscriber management module 145 and a database 146, wherein the database 146 includes, for example, a non-volatile memory (further including a volatile memory). Operations of the communication module 141, the feature analysis module 142, the search engine 143, the dialogue module 144 and the subscriber management module 145 may be implemented by a central processing unit (CPU) or microcontroller (MCU) using software and/or hardware, and the communication module 141, the feature analysis module 142, the search engine 143, the dialogue module 144 and the subscriber management module 145 are coupled with the database 146 for data accessing. The method of data accessing to and from a memory by CPU or MCU is known to the art and thus details thereof are not repeated herein. In addition, the database 146 may further include an external memory.

The communication module 141 communicates, using application software, with a plurality of user end devices 121-12N via the internet 16 so as to receive requests and physiological measurement information from the user end devices 121-12N, and send content information to the user end devices 121-12N. In this embodiment, the application software is directly provided by the interactive service platform 14 to the user end devices 121-12N for installation, or provided to other websites/web domains from the interactive service platform 14 for being downloaded and installed by the user end devices 121-12N, or provided by other suppliers of internet content without particular limitations. After the application software is installed on the user end devices 121-12N, the user end devices 121-12N are able to log in and use the interactive service platform 14.

In the present disclosure, the requests are referred to the information sent from each of the user end devices 121-12N to the interactive service platform 14 and expected to be replied, and the content information is referred to the information replied by the interactive service platform 14 and sent to the user end devices 121-12N for responding the requests.

The feature analysis module 142 analyzes the physiological measurement information to identify at least one of a physiological state, an emotion state, a lifestyle, habits, likes and dislikes of associated subscribers (i.e. subscribes providing the physiological measurement information) and generate an analyzed result, wherein the analyzed result is stored in the database 146 and associated with each corresponding subscriber such that when the analyzed result is inquired by one of the subscribers, the analyzed result is provided to the user end device of the subscriber giving the inquiry. As mentioned above, when the physiological measurement information is a PPG signal, the feature analysis module 142 analyzes the PPG signal to obtain a value variation and/or timeline feature of at least one of a blood oxygenation, a heart rate, a respiration rate, a blood pressure and a second derivative of photoplethysmogram (SDPPG) to be stored in the database 146 and associated with each corresponding subscriber.

Figure 2:
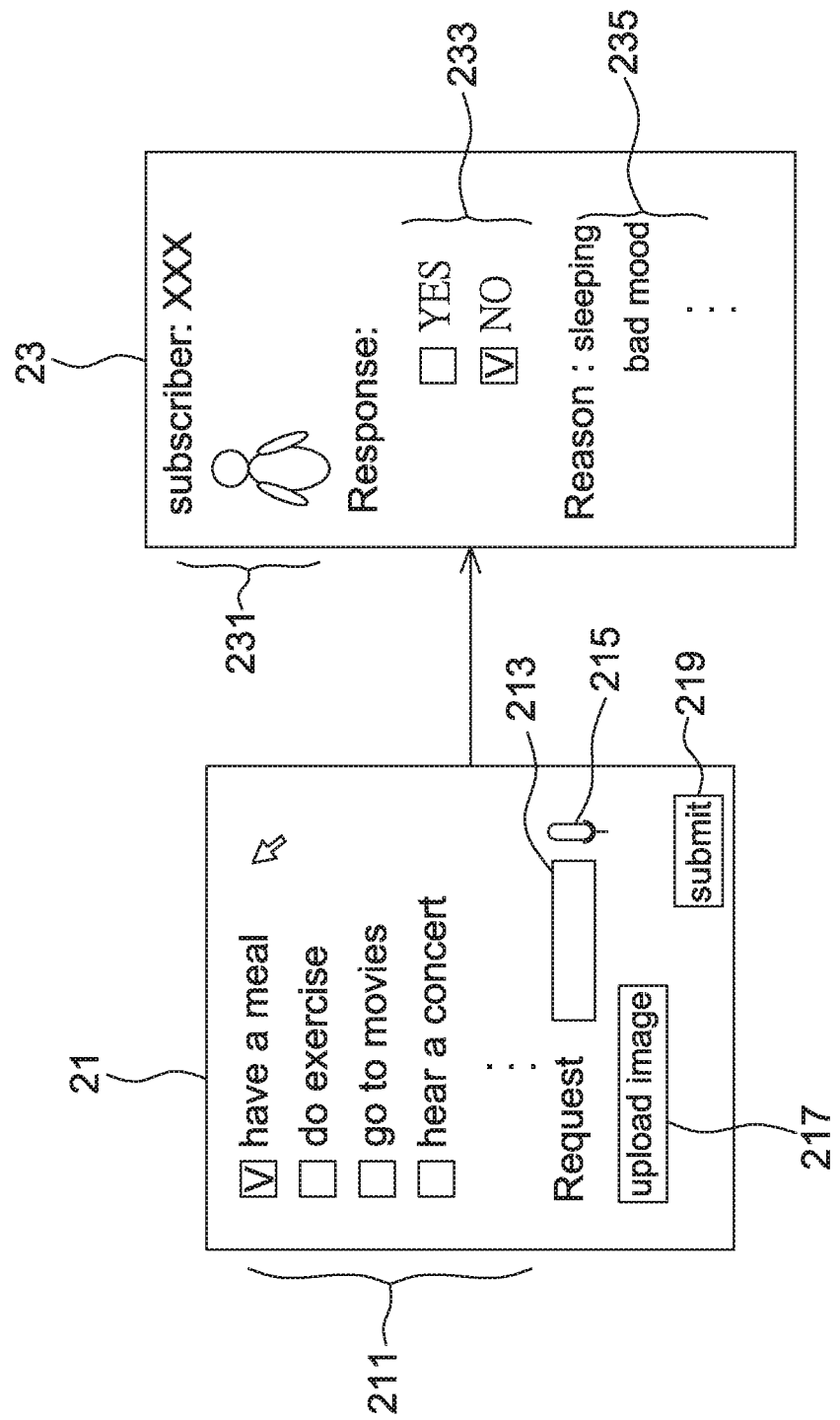
FIG. 2 is a schematic diagram of a request screen and a response screen provided by an interactive service platform according to one embodiment of the present disclosure.

Referring to FIG. 2, it is a schematic diagram of a request screen 21 and a response screen 23 provided by an interactive service platform 14 according to one embodiment of the present disclosure, wherein the request screen 21 is used as one embodiment of the requests and shown on a display screen of the user end devices 121-12N; the response screen 23 is used as one embodiment of the content information and shown on the display screen of the user end devices 121-12N. It should be mentioned that the requests and the content information are not limited to be shown on a screen. In other embodiments, it is possible to present the requests and the content information by words, voices, pictures and/or multimedia according to different applications as long as users are informed by the user end devices 121-12N.

In this embodiment, a request is transmitted to the interactive service platform 14 through a predetermined selection screen of the application software or through an input character string, an image file or an audio file. For example, in FIG. 2 the request screen 21 is shown to include a plurality of predetermined inquiry items 211 for being selected by a user, or include an input block 213 for the user to input an inquiry character string, or include an voice icon 215 for the user to input an inquiry audio file, or include an image upload icon 217 for the user to upload an image file. When the user selects the inquiry items 211, inputs the inquiry character string in the input block 213, finishes the audio input or uploads the image file, a submit icon 219 is clicked to take an input result as the request to be transmitted to the interactive service platform 14 via the internet 16. It is appreciated that items included in the request screen 21 are not limited to those shown in FIG. 2.

After the interactive service platform 14 receives a request, the dialogue module 144 thereof actively responds, according to the request from the user end devices 121-12N, content information of at least one subscriber (i.e. the inquired subscriber) based on an analyzed result of the physiological measurement information associated with the at least one subscriber, e.g., sending a response screen 23 to the user end device sending the request (i.e. an inquiry subscriber). The response screen 23 in FIG. 2 is shown to include a subscriber image (uploaded by the subscriber or selected from database) and a user ID 231, a first response information 233 and a second response information 235, wherein the first response information 233 and the second response information 235 are, for example, used as a part of the analyzed results. The subscriber image and the user ID 231 represent the inquired subscriber.

In this embodiment, the interactive service platform 14 actively/automatically replying the content information is referred to that the interactive service platform 14 previously gets a permission (authorizing to actively respond) from an associated subscriber (i.e. the inquired subscriber) to directly respond a request from other subscribers (i.e. the inquiry subscriber) according to the analyzed result when the interactive service platform 14 receives the request from said other subscribers without obtaining a real-time permission from the associated subscriber again.

For example, when a request given by a first subscriber 121 is to have a meal together and the dialogue module 144 knows, according to the analyzed result stored in the database 146, that an inquired subscriber (e.g., anyone of the user end devices 121-12N) is in sleeping or tired, the dialogue module 144 actively responds "NO" as the first response information 233 according to the analyzed result, and also selects a reason as the second response information 235. It should be mentioned that, in this embodiment, the content information is referred to an active response from the interactive service platform 14 according to the analyzed result as a reference for an user of the first user end device 121 to decide whether to make an appointment with the inquired subscriber, but is not referred to that a user of the inquired subscriber has been actually inquired.

Of course, the user of the first user end device 121 is still able to make an appointment with the user of the inquired subscriber without considering the active response since it is personal will of the user of the first user end device 121. In the present disclosure, the active response from the interactive service platform 14 is used as a reference for the user of the first user end device 121 to know whether it is appropriate to make an appointment before he/she is going to actually contact the users of other user end devices 122-12N.

The database 146 is used to store physiological measurement information of a plurality of users and an analyzed result of the physiological measurement information corresponding to each of the subscribers for other modules of the interactive service platform 14 to access or update. When the communication module 141 receives new physiological measurement information, the stored content in the database 146 is updated, e.g., updating the physiological measurement information and analyzed results.

In some embodiments, when a request is picked from the inquiry items 211, the interactive service platform 14 already knows what kind of analyzed results may be previously stored and thus the database 146 further stores linkage information associated with the value variation and/or timeline feature with respect to the physiological state, the emotion state and the lifestyle, wherein the linkage information includes, for example, a machine learning algorithm which classifies and identifies associated subscribers according to the value variation and/or the timeline feature. For example, the feature analysis module 142 is able to analyze physical and mental states, which are stored in the database 146, of each subscriber at different times of every day according to the received physiological measurement information, and continuously perform the learning and classifying based on new physiological measurement information. When the interactive service platform 14 receives a request, the dialogue module 144 knows the state of the inquired subscriber at the inquired time (e.g., obtained from system time or from internet) according to the analyzed result and actively makes a response, e.g., sending the response screen 23 or providing the response by words, voices, pictures and/or multimedia to the user end device of the subscriber giving the inquiry (i.e. inquiry subscriber).

In other embodiments, if a request is not predetermined but decided by an inquiry subscriber (e.g., by inputting character string or voice file), it is possible that the interactive service platform 14 does not store the corresponded analyzed result. In this case, the interactive service platform 14 uses the search engine 143 to search, on the internet 16 using a text mining technique, linkage information associated with the value variation and/or timeline feature with respect to the physiological state, the emotion state and the lifestyle to be stored in the database 146. When the interactive service platform 14 receives the request, the dialogue module 144 actively gives a response according to the result of the text mining, e.g., sending the response screen 23 or providing the response to a user end device of the inquiry subscriber by words, voices, pictures or multimedia.

The text mining is an operation to retrieve knowledge from large amount of data and is broadly used in data analysis. Although different results are obtainable according to different analyzed targets, the processing procedure is substantially unchanged. The text mining mainly includes data selection, pre-processing, data transformation, data mining, interpretation or evaluation.

Data selection: Data selection is to understand the knowledge of a specific field (e.g., physiological measurement field) and select the data associated with an analyzed target to construct target data sets so as to focus on the selected data subset during text mining.

Pre-processing: Data in the data sets may include errors, data loss and incomplete data which should be removed so as to cancel the influence from the interference and inconsistent data. Pre-processing also processes data of different data formats to make the processed data have a consistent data format.

Data transformation: Data transformation is to perform the data simplification and transformation and analyze big data to find useful information. When a huge amount of calculation is required, it is possible to properly reduce the data amount, e.g., using dimension reduction, transformation, encoding or the like.

Data mining: The most important step in the whole processing procedure. Algorithms are used to analyze data to find hidden features and rules, including data clustering, data classification, association rule, decision tree, statistics regression or the like.

Interpretation/Evaluation: The feature and model found in the data mining are converted to graphs easily to be understood using graphic tool for being used in determination, and the converted result is stored and displayed by a format (e.g., metadata) which can be displayed by the used application software, e.g., stored in the database 146 or showing on a display screen of the user end devices 121-12N.

The text mining technique is to dig out novel and useful information from the data to be analyzed. The typical text mining includes the categorization, clustering and concept/entity extraction.

If it is desired to automatically classify documents, e.g., classifying documents into entertainments, sport habits, eating habits, life habits and so on, said documents may be firstly sent into Lucene to construct the index structure and then acquire vectors representing each document (referred to Term Vector in Lucent). After the Term Vectors are obtained, the Term Vectors of each document are used as an input of a classification algorithm. After being calculated by the machine learning classification algorithm, the classified result is then obtainable. For example, the relationship of the value variation and timeline feature of the physiological measurement information and subscriber's personal data to the physiological state, emotion state, lifestyle, favorite and personality, and thus it is possible to classify subscribers and identify the physical and mental state/lifestyle of subscribers.

In the application of the text mining, the machine learning algorithm is generally used such as automatic document classification or automatic clustering. For example, it is possible to use the machine learning program such as Mahout under the Apache Software Foundation to perform kernel algorithms such as the clustering, classification and collaborative filtering to calculate the desired results.

The above described text mining technique explains a substantial procedure, and as it is known to the art, details thereof are not described herein. The present disclosure uses the value variation and/or timeline feature of the physiological measurement information and the subscriber's personal data as the analyzed target in order to obtain at least one of the physiological state, emotion state, lifestyle, personality and favorite of associated subscribers by using text mining technique. Accordingly, each subscriber is able to understand him/herself or other subscribers by using the interactive service platform 14 of the present disclosure to improve the ability of life planning and social skills.

In addition to analyzing the physiological measurement information and identifying the physical and mental state/lifestyle of associated subscribers, the interactive service platform 14 is further used to analyze subscriber's personal data being authorized for identifying the personality and favorite of associated subscribers (e.g., authorized subscribers) as a part of the content information. The subscriber's personal data includes information of various digital content such as information on at least one of social networking sites, communication software, game dialogue, contacts, positioning systems (GPS), visited websites, search keywords, emails, pictures, contributions and papers. For example, the interactive service platform 14 has the function of a collector for searching, by the search engine 143, the subscriber's personal data on the internet 16 using the text mining technique to accordingly identify the personality and favorite of the associated subscribers (i.e. authorized subscribers). For example, the interactive service platform 14 knows favorite food and entertainment of the associated subscribers according to the reserved restaurants and movies, and knows the personality of the associated subscribers according to the visited websites, inputted search keywords, played game types or the like. The analyzed results of the personality and favorite are also stored in the database 146 for being accessed by the dialogue module 144 at the time giving an active response.

Accordingly, when an inquiry subscriber would like to invite an inquired subscriber or give a gift to the inquired subscriber, it is possible to take the active response from the interactive service platform 14 as a reference to choose a better time or gift.

The subscriber management module 145 is used to record the subscriber's personal data, e.g., ID data and usage setting, wherein said subscriber's personal data is substantially stored in the database 146. The subscriber management module 145 may further include a volatile memory such that when one subscriber logs in, the subscriber's personal data of the login subscriber is read from the database 146 to be temporarily stored in the volatile memory. When the subscriber logs out, the updated subscriber's personal data is stored back into the database 146.

Figure 3:
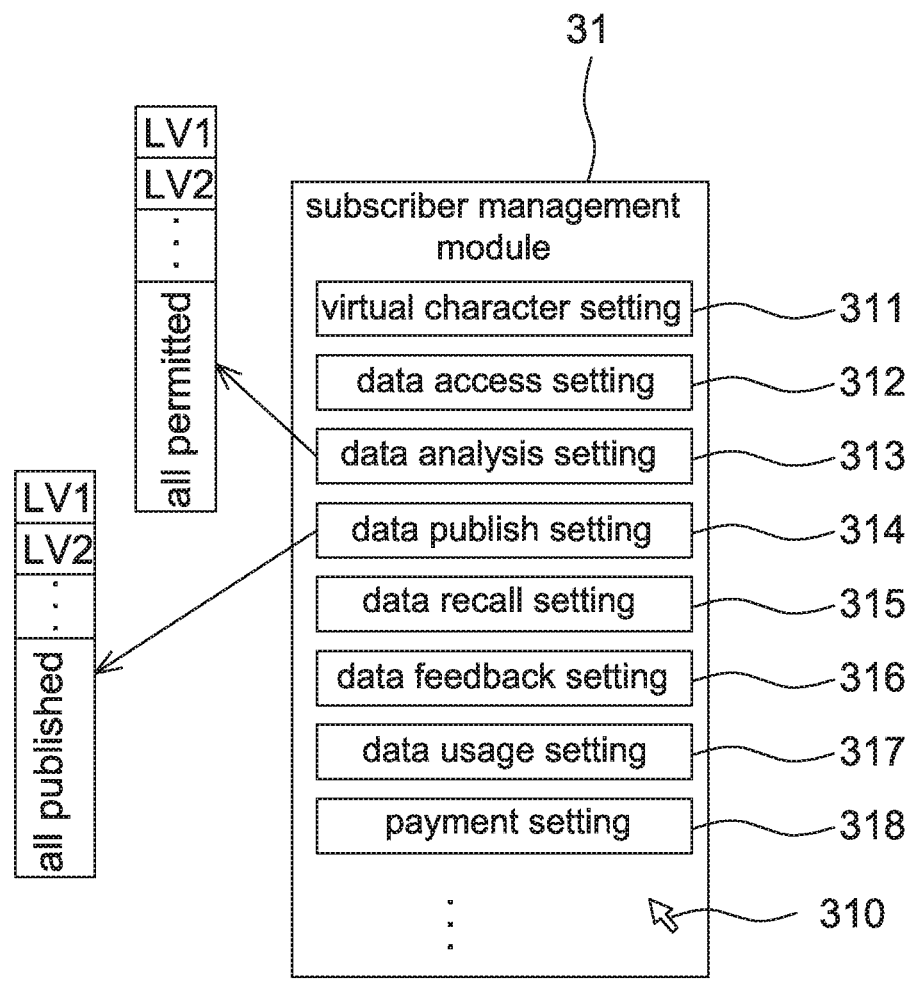
FIG. 3 is a schematic diagram of a subscriber setting screen provided by an interactive service platform according to one embodiment of the present disclosure.

For example, FIG. 3 shows that the subscriber management module 145 provides a subscriber setting screen 31 which is applicable to the user end devices 121-12N having a display screen. The subscriber setting screen 31 includes, for example, at least one of a virtual character setting 311, a data access setting 312, a data analysis setting 313, a data publish setting 314, a data recall setting 315, a data feedback setting 316, a data usage setting 317 and a payment setting 318, but not limited thereto.

Virtual character setting 311: To use the interactive service platform 14, each user end device needs to install associated application software and log in to become a subscriber (or member) through the application software. During login, each user selects a virtual character to represent him/herself for interacting with other subscribers. For example, each user may upload a photo by him/herself or select a predetermined image, and decide a user ID 231 to be used by the virtual character, wherein the user may set the appearance, style, personality and voice of the virtual character to allow the virtual character to similar to him/herself as much as possible. The virtual character performs so-called active interaction with other subscribers (e.g., authorized subscriber) based on an authorized range without a real-time response from the user each time.

For example, when a subscriber logs in the interactive service platform 14, the login subscriber is able to chat with other subscribers. However, the one to whom the login subscriber talks is a virtual character on the interactive service platform 14 but not an actual user constructing the virtual character. This is different from real-time communication software.

Data access setting 312: A user may authorize the interactive service platform 14 to access user data, e.g., including non-autonomic inputted data (e.g., physiological measurement information) and autonomic inputted data (e.g., sports information, social application information, pictures, GPS data, calling information, voices of user) of other software in the user end devices 121-12N through the installed application software. The autonomic inputted data herein is referred to that can be thought controlled by a user, and the non-autonomic inputted data herein is referred to that cannot be thought controlled by a user.

Data analysis setting 313: A user may authorize application software (i.e. installed on the interactive service platform 14) to construct identified results regarding physical and mental state of subscriber by analyzing physiological measurement information and subscriber's personal data of the user. In some embodiments, the interactive service platform 14 divides the analysis authorization into several levels such as LV1, LV2 . . . and so on. For example, it is possible that a user freely selects a level that he/she wants, e.g., authorizing the analyzation of autonomic inputted data but refusing the analyzation of non-autonomic inputted data, or authorizing the analyzation of all data. The level setting is, for example, previously set by the application software. The analyzed data is more if the level is set higher/lower.

Data publish setting 314: A user may authorize the application software to publish at least a part of the identified results by the application software (e.g., published on the interactive service platform 14 or other platforms or websites). Similarly, it is possible that the interactive service platform 14 divides the publish authorization into several levels LV1, LV2 . . . and so on. The level setting is, for example, previously set by the application software. The published data is more if the level is set higher/lower.

In some embodiments, the interactive service platform 14 may have an exchange mechanism in the function of the data publish setting 314 to allow subscribers having identical publish authorization levels to exchange the analyzed results or subscriber's personal data. For example, only a scriber authorizing the publication of analyzed results of the physiological state is able to acquire analyzed results of the physiological state of other subscribers through the interactive service platform 14. For example, a subscriber not authorizing the publication of analyzed results of the emotion state is not allowed to acquire analyzed results of the emotion state of other subscribers through the interactive service platform 14. In addition, it is possible that a user changes his/her authorization at each login, e.g., changing the authorized subscriber's personal data and/or analyzed results to not being authorized.

Data recall setting 315: After the data and/or analyzed results in the database 146 are sent to other subscribers through the interactive service platform 14, it is possible that the associated user performs a function of the data recall setting 315 of the interactive service platform 14 to withdraw the transmitted data and/or analyzed results from said other subscribers.

Data feedback setting 316: A user may authorize the interactive service platform 14 to feedback analyzed results which include the results, such as words, voices, images, graphs, internet data or the like, of analyzing physiological measurement information or subscriber's personal data.

Data usage setting 317: A user may authorize the interactive service platform 14 to authorize more than one user end devices to log in one user ID and use at least a part of data and/or analyzed results in the database 146, or authorize only one user end device to be able to log in one user ID.

Payment setting 318: If the interactive service platform 14 is arranged as a payment service platform, users are allowed to set information of the payment account. In some embodiments, a part of services of the interactive service platform 14 are set as payment services. Users are allowed to set the willingness to pay and a level of the willingness to pay using the subscriber setting screen 31. It is possible that different usage levels are permitted according to different payment.

Figure 4:
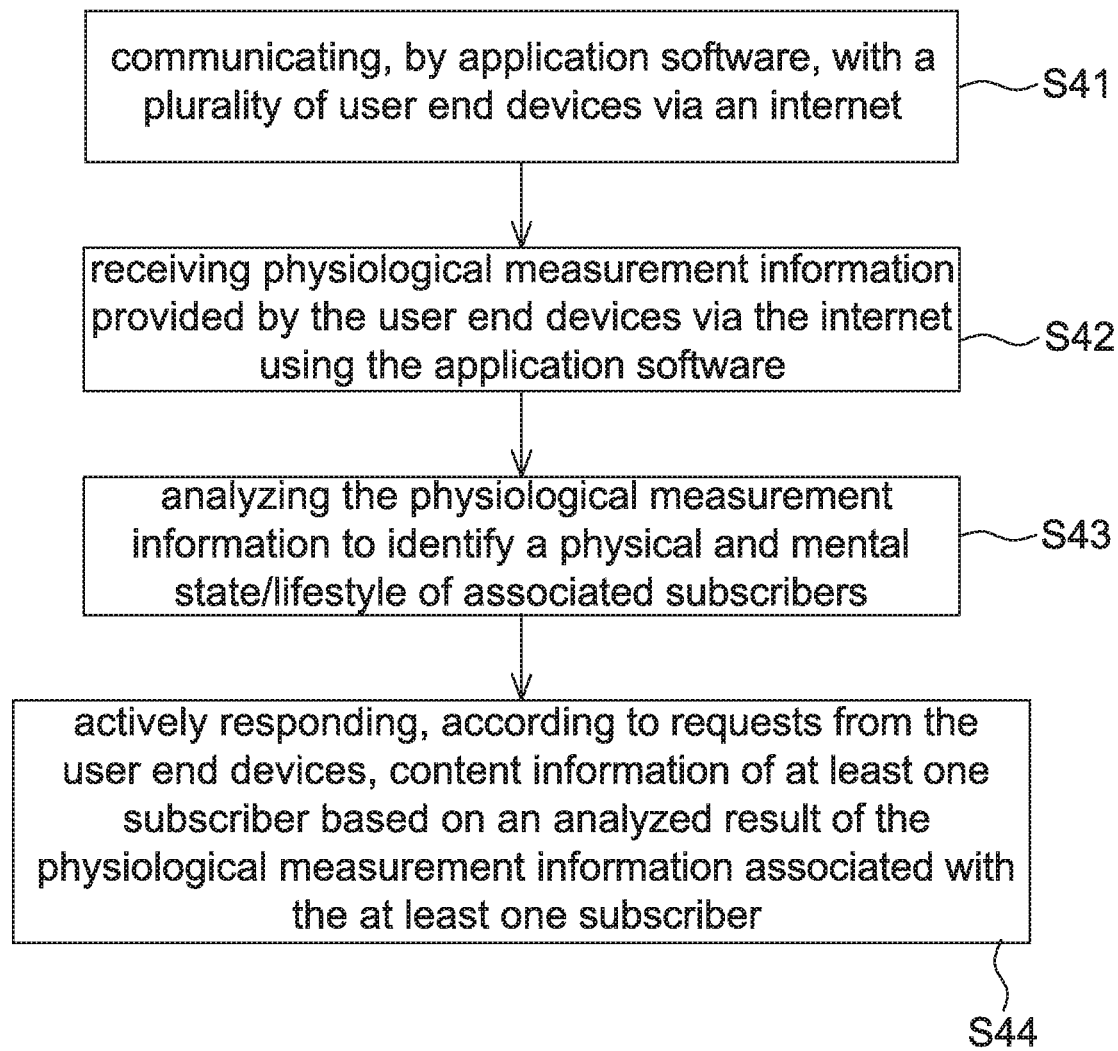
FIG. 4 is a flow chart of an operating method of an interactive service platform according to one embodiment of the present disclosure.

Referring to FIG. 4, it is a flow chart of an operating method of an interactive service platform according to one embodiment of the present disclosure, which includes the steps of: communicating, by application software, between an interactive service platform and a plurality of user end devices via an internet (Step S41); receiving, by the interactive service platform, physiological measurement information provided by the user end devices via the internet using the application software (Step S42); analyzing, by the interactive service platform, the physiological measurement information to identify a physical and mental state/lifestyle of associated subscribers (Step S43); and actively responding, according to requests from the user end devices, content information of at least one subscriber based on an analyzed result of the physiological measurement information associated with the at least one subscriber (Step S44).

Referring to FIGS. 1-4, details of this embodiment are described below.

Step S41: As mentioned above, application software is directly provided by the interactive service platform 14 (as shown in FIG. 1) or from other websites/web domains. The application software is firstly installed on a plurality of user end devices 121-12N, and then the user end devices 121-12N are able to login to become a subscriber (member) and use its services through the application software.

Step S42: In one embodiment, the interactive service platform 14 classifies subscribers or identifies an inquired subscriber through analyzing physiological measurement information. Accordingly, the interactive service platform 14 asks each subscriber to provide the physiological measurement information. As mentioned above, the physiological measurement information includes at least one of a PPG signal and voiceprint data. The interactive service platform 14 actively/automatically receives the physiological measurement information from each of the user end devices 121-12N via the internet 16 continuously or every a predetermined time interval.

Step S43: The feature analysis module 142 of the interactive service platform 14 analyzes the physiological measurement information, e.g., analyzing the PPG signal to obtain a value variation and/or timeline feature of at least one of a blood oxygenation, a heart rate, a respiration rate, a blood pressure and SDPPG, to identify a physiological state, an emotion state and/or a lifestyle of associated subscribers (i.e. subscribers providing the physiological measurement information) to represent the physical and mental state/lifestyle of the associated subscribers. In some embodiments, the interactive service platform 14 pre-stores (e.g., in the database 146) linkage information associated with the value variation and/or the timeline feature with respect to the physiological state, the emotion state and the lifestyle, and the feature analysis module 142 obtains the analyzed result (e.g., subscriber classification or response message shown in FIG. 2) according to the linkage information. In other embodiments, the interactive service platform 14 searches the linkage information associated with the value variation and/or the timeline feature with respect to the physiological state, the emotion state and the lifestyle on the internet 16 using the text mining technique, and obtains the analyzed result according to the linkage information. The linkage information searched from the internet 16 is then stored in the database 146. The interactive service platform 14 has the machine learning algorithm to learn the relationship of the value variation and/or the timeline feature to the physiological state, the emotion state and the lifestyle according to the searched data.

Step S44: As shown in FIG. 2, when the interactive service platform 14 receives requests (e.g., request screen 21) from the user end devices 121-12N, the dialogue module 144 generates content information (e.g., response screen 23) associated with the inquired subscriber according to the analyzed result obtained in Step S43. As mentioned above, it is possible to provide the content information to the user end devices 121-12N by other ways without being limited to that shown in FIG. 2.

The operating method of the interactive service platform 14 further includes a step of subscriber setting for the users to create a subscriber and log in the interactive service platform 14, wherein the subscriber setting is entered every time a subscriber logs in. For example, the interactive service platform 14 provides a subscriber setting screen 31 to the user end devices 121-142N, wherein the subscriber setting screen 31 includes at least one of the virtual character setting, data access setting, data analysis setting, data publish setting, data recall setting, data feedback setting, data usage setting and payment setting, as shown in FIG. 3. It is possible to perform the subscriber setting by using a cursor 310 to click on each setting icon.

In another embodiment, the interactive service platform 14 analyzes subscriber's personal data of other subscribers to analyze the personality and favorite of each subscriber. Accordingly, the operating method of the interactive service platform 14 further includes: inquiring, by the application software, whether the user end devices 121-12N authorize the interactive service platform 14 to actively analyze the subscriber's personal data. If the authorization is agreed by the user end devices 121-12N, the interactive service platform 14 analyzes the authorized subscriber's personal data to identify the personality and favorite of associated subscribers as a part of the content information.

As mentioned above, the subscriber's personal data includes information external to the interactive service platform 14, e.g., information on at least one of social networking sites, communication software, game dialogue, contacts, positioning systems, visited websites, search keywords, emails, pictures, contributions and papers, wherein the interactive service platform 14 searches these subscriber's personal data on the internet 16 using the text mining technique.

Figure 5:
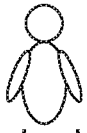
FIGS. 5-6 are schematic diagrams of data setting screens provided by an interactive service platform according to some embodiments of the present disclosure.

In other embodiments, it is possible that a user selects by him/herself whether to authorize the interactive service platform 14 to automatically receive physiological measurement information and/or subscriber's personal data. For example referring to FIG. 5, the interactive service platform 14 provides a data setting screen 51 to the user end devices 121-12N for the users to select by themselves. The data setting screen 51 is entered, for example, when a user uses a cursor 310 shown in FIG. 3 to click on an icon of the data analysis setting 313. In other words, the interactive service platform 14 of the present disclosure 14 may analyze the favorite and personality of users according to the subscriber's personal data but does not analyze the physiological state, emotion state and lifestyle according to the physiological measurement information depending on the authorization from the users.

In some embodiments, the interactive service platform 14 replies autonomic inputted subscriber's personal data to respond a request from an inquiry subscriber. The autonomic inputted subscriber's personal data includes answers that an inquired subscriber non-periodically or periodically replies predetermine inquiry items (e.g., interest, dreams, view of values, activities and so on) automatically provided by the interactive service platform 14 and/or requests automatically provided by other subscribers (e.g., inquiry subscribers) through the interactive service platform 14, and these answers are continuously accumulated to the subscriber's personal data of the inquired subscriber as content information in active response, wherein the autonomic inputted subscriber's personal data is also stored in the database 146 and the predetermined inquiry items may be updated continuously by the interactive service platform 14, e.g., according to different requests from inquiry subscribers. The autonomic inputted subscriber's personal data may be set as authorized subscriber's personal data by a user (e.g., in the data publish setting 314), and when some other subscribers become authorized subscribers (e.g., friend) of the user, the authorized subscriber's personal data is provided to the authorized subscribers automatically. In some embodiments, the authorized subscriber's personal data of a user is provided to the authorized subscribers when the authorized subscribers are talking to the virtual character represent the user.

Figure 7:
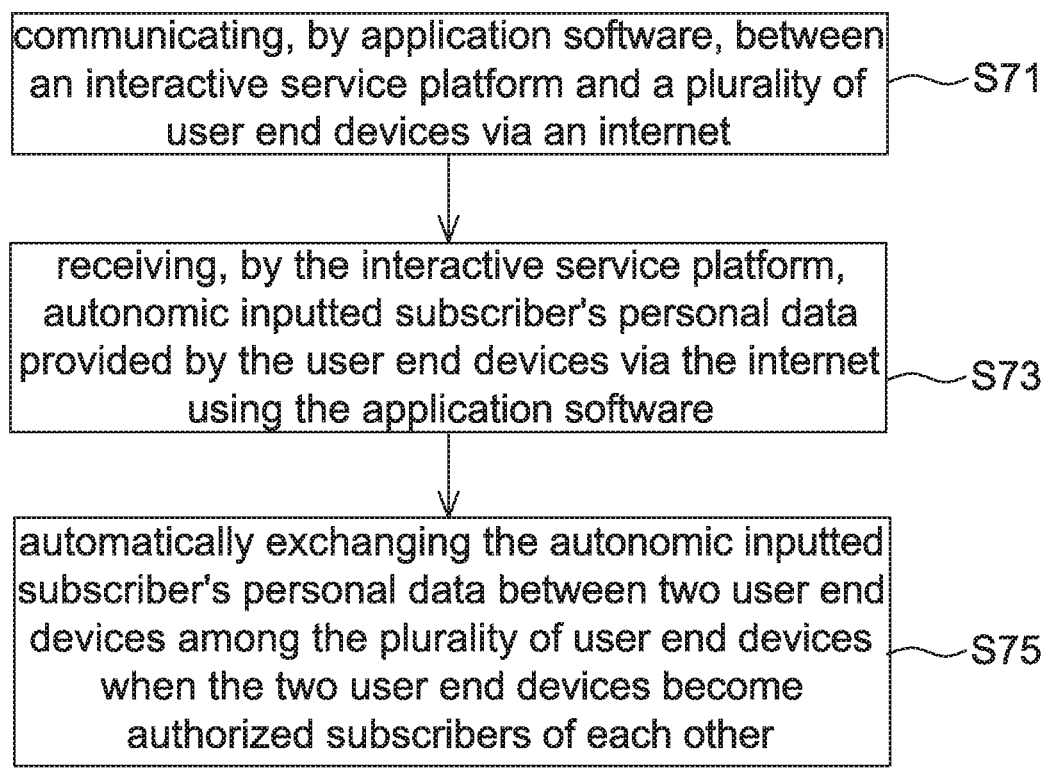
FIG. 7 is a flow chart of an operating method of an interactive service platform according to another embodiment of the present disclosure.

Accordingly, an operating method of an interactive service platform according to another embodiment of the present disclosure is shown in FIG. 7 which includes the steps of, communicating, by application software, between the interactive service platform 14 and a plurality of user end devices 121-12N via the internet 16 (Step S71); receiving, by the interactive service platform 14, autonomic inputted subscriber's personal data provided by the user end devices 121-12N via the internet 16 using the application software (Step S73); and automatically exchanging the autonomic inputted subscriber's personal data between two user end devices among the plurality of user end devices 121-12N when the two user end devices become authorized subscribers of each other (Step S75). In some embodiments, the autonomic inputted subscriber's personal data is used as the content information of the virtual character of the interactive service platform 14 to actively respond the requests from other subscribers (i.e. inquiry subscribers). As mentioned above, the autonomic inputted subscriber's personal data is periodically or not-periodically provided by the scribers using the application software.

The difference between this embodiment and FIG. 4 is that in FIG. 4 the interactive service platform 14 provides mainly the non-autonomic inputted subscriber's personal data (e.g., analyzed results of physiological measurement information) between a plurality of user end devices 121-12N as the content information of the virtual character; whereas in FIG. 7, the interactive service platform 14 provides mainly the autonomic inputted subscriber's personal data between a plurality of user end devices 121-12N as the content information of the virtual character, and details of the operating method of FIG. 7 is similar to those of FIG. 4 and thus are not repeated herein. In addition, the autonomic inputted subscriber's personal data is also built up using some functions in the subscriber setting screen 31 of the subscriber management module 145.

In some embodiments, the interactive service platform 14 stores both the autonomic inputted subscriber's personal data and the non-autonomic inputted subscriber's personal data of subscribers to perform the operating methods of both FIGS. 4 and 7. In other words, in the present disclosure, the interactive service platform 14 may exchange the autonomic inputted subscriber's personal data and the non-autonomic inputted subscriber's personal data automatically when two subscribers become authorized subscribers (or friends) to each other, or provide the autonomic inputted subscriber's personal data and the non-autonomic inputted subscriber's personal data of one subscriber to another subscriber only when the interactive service platform 14 receives a request from the another subscriber to inquire information of the one subscriber.

The present disclosure is to provide a non-realtime interactive service system in which some of responses are responded by the interactive service platform 14 according to the analyzed results and others are responded by the interactive service platform 14 according to the answers replied by the user.

Figure 6:
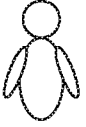

Similarly, after each icon 311-318 shown in FIG. 3 is selected by a cursor 310, the interactive service platform 14 respectively provides a corresponded data setting screen (e.g., as FIG. 6, but not limited thereto), word string, voices or multimedia for being set by the user. It is appreciated that the user end devices 121-12N have corresponding functions, e.g., having a speaker, player or the like.

As mentioned above, conventional on-line service platforms do not have the function of analyzing the current physical and mental state of a user according to physiological measurement information. Therefore, the present disclosure further provides an interactive service system and an interactive service platform (as shown in FIG. 1) and an operating method thereof (as shown in FIGS. 3 and 7) that may automatically identify the subscriber's current physical and mental state as well as lifestyle and actively respond the requests of every subscriber such that each subscriber is able to understand the current physical and mental state as well as lifestyle of every subscriber according the content information actively responded by the interactive service platform.

Although the disclosure has been explained in relation to its preferred embodiment, it is not used to limit the disclosure. It is to be understood that many other possible modifications and variations can be made by those skilled in the art without departing from the spirit and scope of the disclosure as hereinafter claimed.

What is claimed is:

1. An operating method of an interactive service platform, which is installed on a server system connecting to an internet, the operating method comprising:
   communicating, by application software, between the interactive service platform and a plurality of user end devices, each having a display screen, via the internet;
   receiving, by the interactive service platform, physiological measurement information about a plurality of subscribers associated with the plurality of user end devices, wherein the physiological measurement information is provided by the user end devices via a communication network included in the internet using the application software;
   analyzing, by the interactive service platform, the physiological measurement information to identify at least one of a physiological state, an emotion state and a lifestyle of the plurality of subscribers;
   receiving, by the interactive service platform, a permission from a first subscriber among the plurality of subscribers that permits the interactive service platform to directly and automatically respond to a different, second subscriber among the plurality of subscribers; and
   in response to a request received by the interactive service platform from the user end device associated with the second subscriber,
      automatically sending, by the interactive service platform and to the user end device associated with the second subscriber, content information about the first subscriber based on an analyzed result of the physiological measurement information associated with the first subscriber, without obtaining an actual response from the first subscriber to reduce network traffic between the interactive service platform and the user end device associated with the first subscriber, and
      causing the automatically sent content information about the first subscriber to be shown on the display screen of the user end device associated with the second subscriber.

2. The operating method as claimed in claim 1, wherein the physiological measurement information comprises at least one of a photoplethysmography signal and voiceprint data, and
   the user end device of the first subscriber further comprises a light source and a light sensor, wherein the light source is configured to illuminate a skin surface and the light sensor is configured to detect light from the skin surface to generate the photoplethysmography signal.

3. The operating method as claimed in claim 2, wherein the analyzing comprises analyzing the photoplethysmography signal to obtain a value variation and a timeline feature of at least one of a blood oxygenation, a heart rate, a respiration rate, a blood pressure and a second derivative of photoplethysmogram.

4. The operating method as claimed in claim 3, wherein the interactive service platform previously stores linkage information of the value variation and the timeline feature with respect to the physiological state, the emotion state and the lifestyle, and obtains the analyzed result according to the linkage information.

5. The operating method as claimed in claim 3, wherein the analyzing further comprises:
   searching, on the internet by a text mining, linkage information of the value variation and the timeline feature with respect to the physiological state, the emotion state and the lifestyle, and
   obtaining the analyzed result according to the linkage information.

6. The operating method as claimed in claim 1, wherein the request is transmitted to the interactive service platform through a predetermined selection screen of the application software or through an input character string, an image file or an audio file.

7. The operating method as claimed in claim 1, further comprising:
   providing, by the interactive service platform, a subscriber setting screen to the user end devices, wherein the subscriber setting screen comprises at least one of a virtual character setting, a data access setting, a data analysis setting, a data publish setting, a data recall setting, a data feedback setting, a data usage setting and a payment setting.

8. The operating method as claimed in claim 1, further comprising:
   receiving, by the interactive service platform, an authorization of actively analyzing subscriber's personal data from the user end devices through the application software; and
   analyzing the authorized subscriber's personal data to identify personality and favorite of the plurality of subscribers as a part of the content information.

9. The operating method as claimed in claim 8, wherein the subscriber's personal data comprises information of at least one of social networking sites, communication software, game dialogue, contacts, positioning systems, visited websites, search keywords, emails, pictures, contributions and papers, and
   the interactive service platform further searches the subscriber's personal data on the internet using a text mining to accordingly identify the personality and the favorite of the plurality of subscribers.

10. An interactive service platform, which is installed on a server system connecting to an internet, the interactive service platform comprising:
    a communication module configured to communicate with a plurality of user end devices, each having a display screen, via the internet to receive photoplethysmography signals about a plurality of subscribers associated with the plurality of user end devices, wherein the photoplethysmography signals are provided from the user end devices via a communication network included in the internet;
    a feature analysis module configured to analyze the photoplethysmography signals to identify at least one of a physiological state, an emotion state and a lifestyle of the plurality of subscribers;
    a database configured to store
       the photoplethysmography signals of the plurality of subscribers,
       an analyzed result of the photoplethysmography signals corresponding to each of the plurality of subscribers, and a permission, received through the communication module, from a first subscriber among the plurality of subscribers that permits the interactive service platform to directly and automatically respond to a different, second subscriber among the plurality of subscribers; and a dialogue module configured to, in response to a request received through the communication module from the user end device associated with the second subscriber, automatically send, to the user end device associated with the second subscriber, the content information about the first subscriber based on the analyzed result of the photoplethysmography signals associated with the first subscriber, without obtaining an actual response from the first subscriber to reduce network traffic between the interactive service platform and the user end device associated with the first subscriber, wherein the automatically sent content information about the first subscriber is to be shown on the display screen of the user end device associated with the second subscriber.

11. The interactive service platform as claimed in claim 10, wherein the feature analysis module is configured to analyze the photoplethysmography signals to obtain a value variation and a timeline feature of at least one of a blood oxygenation, a heart rate, a respiration rate, a blood pressure and a second derivative of photoplethysmogram.

12. The interactive service platform as claimed in claim 11, wherein
the database is further configured to store linkage information of the value variation and the timeline feature with respect to the physiological state, the emotion state and the lifestyle, and
the feature analysis module is further configured to obtain the analyzed result according to the linkage information.

13. The interactive service platform as claimed in claim 11, further comprising a search engine, wherein
the search engine is configured to search, on the internet using a text mining, linkage information of the value variation and the timeline feature with respect to the physiological state, the emotion state and the lifestyle to be stored in the database, and
the feature analysis module is further configured to obtain the analyzed result according to the linkage information.

14. The interactive service platform as claimed in claim 10, further comprising a subscriber management module configured to provide a subscriber setting screen to the user end devices through the communication module, and the subscriber setting screen comprises at least one of a visual character setting, a data access setting, a data analysis setting, a data publish setting, a data recall setting, a data feedback setting, a data usage setting and a payment setting.

15. The interactive service platform as claimed in claim 10, wherein the feature analysis module is further configured to analyze authorized subscriber's personal data to identify personality and favorite of the plurality of subscribers as a part of the content information.

16. The interactive service platform as claimed in claim 15, wherein
the subscriber's personal data comprises information of at least one of social networking sites, communication software, game dialogue, contacts, positioning systems, visited websites, search keywords, emails, pictures, contributions and papers, and the interactive service platform further comprises a search engine configured to search the subscriber's personal data on the internet using a text mining to accordingly identify the personality and the favorite of the plurality of subscribers.

17. An interactive service system, comprising:
a plurality of user end devices each having a display screen; and
an interactive service platform installed on a server system connecting to an internet, and configured to
receive, by application software, physiological measurement information about a plurality of subscribers associated with the plurality of user end devices, wherein the physiological measurement information is provided from the user end devices via a communication network included in the internet,
analyze the physiological measurement information to identify a physical and mental state as well as a lifestyle of the plurality of subscribers,
receive a permission from a first subscriber among the plurality of subscribers that permits the interactive service platform to directly and automatically respond to a different, second subscriber among the plurality of subscribers, and
in response to a request received from the user end device associated with the second subscriber,
automatically send, to the user end device associated with the second subscriber, content information about the first subscriber based on an analyzed result of the physiological measurement information associated with the first subscriber, without obtaining an actual response from the first subscriber to reduce network traffic between the interactive service platform and the user end device associated with the first subscriber,
wherein the user end device associated with the second subscriber is configured to show, on the display screen thereof, the content information about the first subscriber automatically sent from the interactive service platform.

18. The interactive service system as claimed in claim 17, wherein the user end devices are
built-in with a physiological measurement function configured to measure the physiological measurement information, and
configured to provide the measured physiological measurement information to the interactive service platform via the internet.

19. The interactive service system as claimed in claim 17, wherein the user end devices are
coupled to a physiological detection device via a wired or wireless transmission technique to receive the physiological measurement information from the physiological detection device, and
configured to provide the received physiological measurement information to the interactive service platform via the internet.

20. The interactive service system as claimed in claim 17, wherein the interactive service platform is configured to receive the physiological measurement information from the user end devices via the internet continuously or every a predetermined time interval.

21. An operating method of an interactive service platform, which is installed on a server system connecting to an internet, the operating method comprising:

communicating, by application software, between the interactive service platform and a plurality of user end devices, each having a display screen, via the internet;

receiving, by the interactive service platform, autonomic inputted subscriber's personal data about a plurality of subscribers associated with the plurality of user end devices, wherein the subscriber's personal data are provided by the user end devices via a communication network included in the internet using the application software;

receiving, by the interactive service platform, permissions from first and second subscribers which are authorized subscribers of each other among the plurality of subscribers, wherein the permissions permit the interactive service platform to directly and automatically exchange the autonomic inputted subscriber's personal data between the two user end devices associated with the first and second subscribers;

in response to a request received by the interactive service platform from the user end device associated with the second subscriber, automatically sending, by the interactive service platform and to the user end device associated with the second subscriber, content information about the first subscriber based on an analyzed result of the autonomic inputted subscriber's personal data about the first subscriber, without obtaining an actual response from the first subscriber to reduce network traffic between the interactive service platform and the user end device associated with the first subscriber, and causing the automatically sent content information about the first subscriber to be shown on the display screen of the user end device associated with the second subscriber; and in response to a further request received by the interactive service platform from the user end device associated with the first subscriber, automatically sending, by the interactive service platform and to the user end device associated with the first subscriber, content information about the second subscriber based on an analyzed result of the autonomic inputted subscriber's personal data about the second subscriber, without obtaining an actual response from the second subscriber to reduce network traffic between the interactive service platform and the user end device associated with the second subscriber, and causing the automatically sent content information about the second subscriber to be shown on the display screen of the user end device associated with the first subscriber.

22. The operating method as claimed in claim 21, wherein the autonomic inputted subscriber's personal data comprises answers of a subscriber periodically or non-periodically replying at least one of inquiry items provided by the interactive service platform and requests provided by other subscribers via the interactive service platform.

* * * * *